United States Patent
Stelter et al.

(10) Patent No.: US 12,004,969 B2
(45) Date of Patent: Jun. 11, 2024

(54) METHOD FOR PRODUCING A BREAST PROSTHESIS HAVING AN ADJUSTABLE VOLUME

(71) Applicant: AMOENA MEDIZIN-ORTHOPÄDIE-TECHNIK GMBH, Raubling (DE)

(72) Inventors: Nils Stelter, Frasdorf (DE); Helmut Wild, Stephanskirchen (DE)

(73) Assignee: AMOENA MEDIZIN-ORTHOPÄDIE-TECHNIK GMBH, Raubling (DE)

( * ) Notice: Subject to any disclaimer, the term of this patent is extended or adjusted under 35 U.S.C. 154(b) by 552 days.

(21) Appl. No.: 17/286,176

(22) PCT Filed: Oct. 16, 2019

(86) PCT No.: PCT/EP2019/078042
§ 371 (c)(1),
(2) Date: Apr. 16, 2021

(87) PCT Pub. No.: WO2020/079049
PCT Pub. Date: Apr. 23, 2020

(65) Prior Publication Data
US 2021/0346177 A1    Nov. 11, 2021

(30) Foreign Application Priority Data
Oct. 18, 2018   (DE) .................. 10 2018 125 897.6

(51) Int. Cl.
A61F 2/50    (2006.01)
A61F 2/52    (2006.01)
(Continued)

(52) U.S. Cl.
CPC .............. *A61F 2/5044* (2013.01); *A61F 2/52* (2013.01); *B29C 66/43* (2013.01); *A61F 2002/501* (2013.01); *B29L 2031/7532* (2013.01)

(58) Field of Classification Search
CPC .... A61F 2/5044; A61F 2/52; A61F 2002/501; A61F 2/5046; A61F 2240/001;
(Continued)

(56) References Cited

U.S. PATENT DOCUMENTS

| | | | | |
|---|---|---|---|---|
| 4,823,815 A | * | 4/1989 | Watson | A61B 90/02 623/8 |
| 2013/0096675 A1 | * | 4/2013 | Sjunnesson | A61F 2/5046 623/7 |
| 2015/0314493 A1 | * | 11/2015 | Stadler | B29C 43/203 264/510 |

FOREIGN PATENT DOCUMENTS

| | | |
|---|---|---|
| CN | 101005807 A | 7/2007 |
| CN | 102949251 A | 3/2013 |

(Continued)

*Primary Examiner* — Cynthia L Schaller
(74) *Attorney, Agent, or Firm* — Dilworth & Barrese, LLP

(57) ABSTRACT

The invention relates to a method for producing a breast prosthesis (1) having an adjustable volume, wherein the breast prosthesis comprises a first shell body (10), a second shell body (20) which is circumferentially connected thereto, and a fluid chamber (30) arranged between the shell bodies, wherein the method comprises the following steps: (a) peripherally connecting four plastic films to provide a template comprising three chambers; (b) filling the upper and lower chambers with a crosslinkable silicone filler; and (c) crosslinking the silicone filler.

15 Claims, 2 Drawing Sheets

(51) Int. Cl.
*B29C 65/00* (2006.01)
*B29L 31/00* (2006.01)

(58) Field of Classification Search
CPC ...... A61F 2240/002; A61F 2/12; B29C 66/43; B29L 2031/7532
See application file for complete search history.

(56) References Cited

FOREIGN PATENT DOCUMENTS

| | | | |
|---|---|---|---|
| CN | 103917193 A | 7/2014 | |
| CN | 105034395 A | 11/2015 | |
| CN | 107212952 A | 9/2017 | |
| DE | 102006035069 A1 | 11/2007 | |
| DE | 102014006313 A1 | 11/2015 | |
| DE | 202015007895 U1 | 2/2017 | |
| EP | 0824001 A2 | 2/1998 | |
| EP | 2944291 A1 | 11/2015 | |
| EP | 3243487 A1 | 11/2017 | |
| WO | 2011/098283 A1 | 8/2011 | |
| WO | 2016/109117 A1 | 7/2016 | |
| WO | WO-2016109117 A1 * | 7/2016 | ........... A61F 2/5046 |

* cited by examiner

METHOD FOR PRODUCING A BREAST PROSTHESIS HAVING AN ADJUSTABLE VOLUME

BACKGROUND OF THE INVENTION

The invention relates to a method of producing a breast prosthesis having an adjustable volume.

Breast prostheses are worn after surgical breast removals. Demands on breast prostheses in particular include a shape and feel that come as close as possible to the natural breast as well as a high comfort in wear.

To be able to accomplish being able to adjust the volume of such a prosthesis to the individual needs of the wearer that result from the size of the still healthy breast, if present, or from personal well-being without expensive custom-made solutions, it has already been proposed in the prior art to provide breast prostheses whose volume can be retroactively adjusted. EP 0 824 001 A2 is to be named as an example for this.

SUMMARY OF THE INVENTION

It is the object of the invention to provide a method of producing a volume-adjustable breast prosthesis having improved properties.

Against this background, the invention relates to a method of producing a breast prosthesis having an adjustable volume, wherein the breast prosthesis has a first shell body, a second shell body peripherally connected thereto, and a fluid space arranged between said shell bodies, the method comprising the following steps: (a) peripherally connecting four plastic films to provide a template comprising three chambers; (b) filling the upper and lower chambers with a crosslinkable silicone compound; and (c) crosslinking the silicone compound.

The shells bodies of the breast prosthesis produced in this manner is therefore a film bag filled with a deformable material. The crosslinkable silicone compound is preferably a two-component silicone compound. After the crosslinking, a crosslinked silicone rubber results from such a compound, preferably two-component silicone rubber. This rubber allows the shell bodies to satisfy the demands on feel and comfort in wear and not to impede an expansion of the fluid space volume.

The crosslinkable silicone compound can comprise additional components such as a phase change material or a porous granulate or hollow spheres. Phase change materials serve the improvement of heat regulation at the skin of the wearer and are therefore preferably admixed to the silicone compound of the first shell body that should lie on the side of the wearer in use. Suitable phase change materials include those whose phase transition temperature is close to body temperature. Examples include paraffins having a suitable number of carbon atoms, typically approximately twenty, to set a melting point in the desired range. Granulates or hollow spheres can serve to reduce the weight of the prosthesis without impairing the haptic properties.

The indications of four films and three chambers are to be understood in the sense of a minimum indication. Variants having more than three chambers are covered by the invention, which would require the connection of more than four films.

The peripheral connection of the four plastic films in accordance with step (a) can be a peripheral welding. Alternatively or additionally, an adhesive bonding along the common peripheral surface could also take place.

Provision can be made that to form access to the respective chamber, an interruption is left free between the two upper films and/or between the two lower films in the course of the peripheral connection of the four plastic films in accordance with step (a). The filling of the upper and/or lower chamber(s) in accordance with step (b) can take place through the interruption.

Provision is preferably made that the crosslinking of the silicone compound takes place by raising the temperature.

The interruption is closed, preferably welded, before or after the crosslinking.

To form radial access to the fluid space, a valve tube can be enclosed between the two middle films as part of the peripheral connection of the four plastic films in accordance with step (a). The tube is adhesively bonded or welded between the films and can thus penetrate the weld seam or adhesive seam between the film bags in the radial direction. The breast prosthesis produced in this manner therefore further comprises a valve tube, composed of a flexible material and preferably a plastic material, that reaches externally into the fluid space in the connection region between the shell bodies and projects beyond the connection region into the fluid space. The valve tube generally has a check valve such as a flutter valve and serves to enable a subsequent filling and emptying of the fluid space, i.e. after the production.

Provision can be made that the method additionally comprises a step of introducing a medium for reducing the adhesive tendency of the oppositely disposed inner surfaces of the shell bodes to the fluid space, with provision preferably being made that the medium for reducing the adhesive tendency of the oppositely disposed inner surfaces of the shell bodies is introduced into the fluid space through the valve tube. A needle can, for example, be pressed into the valve tube and the medium can be pressed into the chamber through this needle.

A breast prosthesis produced in this manner comprises an additional medium that is different from the fluid for the volume adjustment, that reduces the adhesive tendency of the oppositely disposed inner surfaces of the shell bodies, and that is in the fluid space whose filling with a fluid for volume adjustment is intended. The subsequent volume adjustment can be impeded in that the inner surfaces of the shell bodies adhere to one another. A permanent deformation of the breast prosthesis by such an adhesion would also have to be feared. The invention therefore provides reducing the tendency for such an unwanted adhesion.

The medium for reducing the adhesive tendency of the oppositely disposed inner surfaces of the shell bodies can be a liquid, in particular an oil, and further preferably a silicone oil. In the event that both the fluid for the volume adjustment and the medium for reducing the adhesive tendency of the oppositely disposed inner surfaces of the shell bodies are respectively liquids, these liquids differ from one another.

The medium for reducing the adhesive tendency of the oppositely disposed inner surfaces of the shell bodies can furthermore be a powdery solid. The average particle size of the powder grains is preferably in the range between 1 nm to 1 mm. The powder can, for example, be blown into the fluid space in combination with a gas.

The medium for reducing the adhesive tendency of the oppositely disposed inner surfaces of the shell bodies can optionally also be a gas. In the event that both the fluid for the volume adjustment and the medium for reducing the adhesive tendency of the oppositely disposed inner surfaces of the shell bodies are respectively gases, these gases differ from one another.

Combinations of said media for reducing the adhesive tendency of the oppositely disposed inner surfaces of the shell bodies are also used in further embodiments. A mixture of liquids and dispersed powdery solids can be used, for example, with the liquids and dispersed powdery solids being able to be formed as defined above.

Provision is made in a variant that the medium for reducing the adhesive tendency of the oppositely disposed inner surfaces of the shell bodies is introduced before the filling of the upper and lower chambers with a crosslinkable silicone compound in accordance with step (b).

Provision is made in an alternative variant that the medium for reducing the adhesive tendency of the oppositely disposed inner surfaces of the shell bodies is introduced between the filling of the upper and lower chambers with a crosslinkable silicone compound in accordance with step (b) and the crosslinking of the silicone compound in accordance with step (c).

Provision is made in yet another variant that the medium for reducing the adhesive tendency of the oppositely disposed inner surfaces of the shell bodies is introduced after the crosslinking of the silicone compound in accordance with step (c). Step (c) and optionally step (a) and/or the introduction of the medium for reducing the adhesive tendency of the oppositely disposed inner surfaces of the shell bodies preferably take place in a shaping tool. The closing, preferably welding, of the passages for the introduction of the silicone compound into the forming shell bodies can also take place in this shaping tool.

It is intended that the volume of the breast prosthesis is subsequently adjusted, i.e. on the user side, by filling fluid for the volume adjustment into the fluid space. The fluid for the volume adjustment can be a gas, in particular air. The fluid for the volume adjustment can furthermore be a liquid, in particular a subsequently crosslinkable viscous liquid and further preferably a crosslinkable silicone fluid. Combinations are also conceivable.

BRIEF DESCRIPTION OF THE DRAWINGS

Further details and advantages of the invention result from the following embodiment described with reference to the Figures. There are shown in the Figures:

FIG. 3: a chart of a further embodiment variant of a method in accordance with the invention.

DESCRIPTION OF THE PREFERRED EMBODIMENTS

Figure 1:
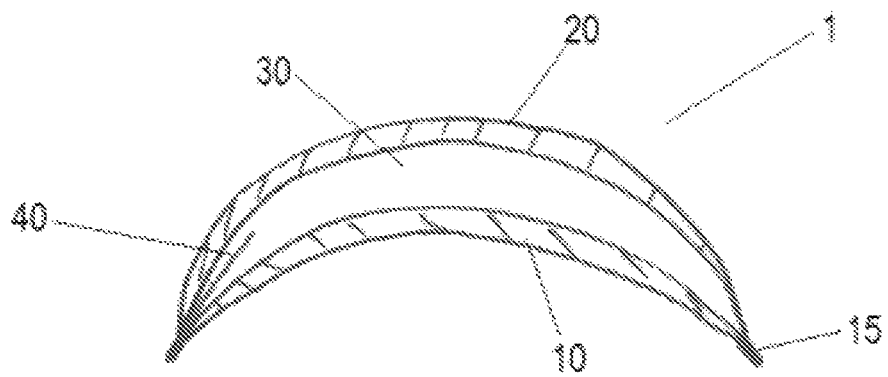
FIG. 1: a schematic representation of a volume-adjustable breast prosthesis produced using the method in accordance with the invention.

The breast prosthesis 1 having an adjustable volume shown in FIG. 1 can be produced using a method in accordance with the invention. The breast prosthesis 1 comprises a first shell body 10 at the lower side of the prosthesis 1 facing the wearer and a second shell body 20 peripherally connected thereto and at the upper side of the prosthesis 1 facing away from the wearer. Both shell bodies 10 and 20 are film bags that are fill with a crosslinked two-component silicone rubber compound. The film bags are each produced from two plastic film pieces that are welded to one another along the common peripheral surface.

The shell bodies 10 and 20 are in turn connected along a peripheral weld seam 15 such that a fluid space 30 is formed between them that can, for example, be filled with air, but also with a liquid. The volume of the breast prosthesis 1 can be adjusted by filling and emptying the fluid space 30.

To make a subsequent filling and emptying of the fluid space 30 possible, i.e. one taking place after the production, the breast prosthesis 1 comprises a valve tube 40 that is composed of a flexible plastic material, that comprises a flat flutter valve, that penetrates the weld seam 15 in the radial direction, and that is welded between the shell bodies 10 and 20 in this process. The valve tube 40 does not only reach up to the end of the weld seam 15, but projects freely, i.e. without being connected to one of the shell bodies 10 or 20, beyond the weld seam 15 into the fluid space 30. The section of the valve tube 40 projecting into the fluid space 30 is therefore freely movable in the fluid space 30.

To prevent a sticking together of the plastic inner surfaces of the two shell bodies 10 and 20 due, for example, to electrostatic interaction and thus an unwanted adhesion of the fluid space 30, the fluid space 30 is filled with a smaller amount of silicone oil.

Figure 2:
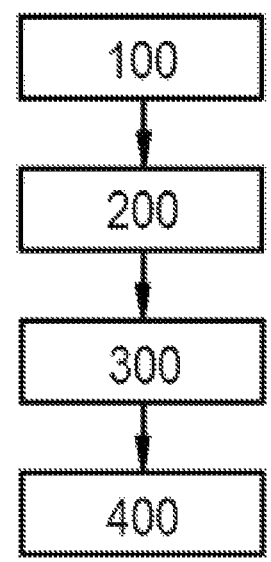
Figure 3:
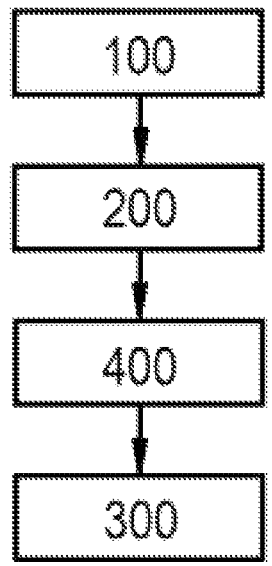
FIG. 3: a chart of an embodiment variant of a method in accordance with the invention.
Figure 4:
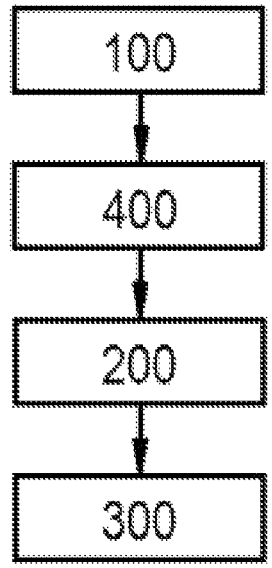
FIG. 4: a chart of yet another embodiment variant of a method in accordance with the invention.

Three variants of possible procedures of a method in accordance with the invention for producing the breast prosthesis 1 shown in FIG. 1 are shown schematically in FIGS. 2-4.

It is common to all the methods that four plastic films for providing a template comprising three chambers are peripherally connected in a first step 100 corresponding to step (a).

In a first variant of the method procedure, such as shown in FIG. 2, a step 200, corresponding to step (b), follows on directly from this, with the upper chamber, i.e. the chamber between the upper two films, and the lower chamber, i.e. the chamber between the upper two films, are filled with a crosslinkable two-component silicone compound. The hardening by the effect of heat in accordance with step 300, corresponding to step (c), then follows. The introduction of the medium for reducing the adhesive tendency of the oppositely disposed inner surfaces of the shell bodies only takes place in a last step 400 subsequent to this step.

In a second variant of the method procedure such as shown in FIG. 3, step 100 is furthermore directly followed by step 200, with the medium for reducing the adhesive tendency of the oppositely disposed inner surfaces of the shell bodies in accordance with step 400, however, taking place before the hardening by the effect of heat in accordance with step 300, corresponding to step (c).

In a third variant of the method procedure such as shown in FIG. 4, step 100 is directly followed by the introduction of the medium for reducing the adhesive tendency of the oppositely disposed inner surfaces of the shell bodies in accordance with step 400. The silicone compound is only subsequently introduced into the upper and lower chambers and hardened in accordance with steps 200 and 300.

The hardening of the silicone compound in accordance with step 300 respectively takes place here in a shaping tool under the effect of temperature. The passages in the weld seams through which the silicone compounds are filled into the upper and lower chambers can be welded in these shaping tools, either before or after hardening.

The invention claimed is:

1. A method of producing a breast prosthesis (1) having an adjustable volume by a user, wherein the breast prosthesis (1) has a first shell body (10), a second shell body (20) peripherally connected thereto, and a fluid space (30)

arranged between said shell bodies (10, 20) and fillable by the user to a desired volume, the method comprising the following steps:
(a) peripherally connecting four plastic films to provide a template comprising three chambers;
(b) filling upper and lower chambers with a crosslinkable silicone compound; and
(c) crosslinking the silicone compound, and
(d) inserting a valve tube (40) between two middle films to form radial access to the fluid space (30) and attaching the valve tube (40) to the prosthesis (1) as part of the peripheral connection of the four plastic films in accordance with step (a).

2. A method in accordance with claim 1, wherein the peripheral connection of the four plastic films in accordance with step (a) is a peripheral welding.

3. A method in accordance with claim 1, wherein, to form access to a respective chamber, an interruption is left free between the two upper films and/or between two lower films during the peripheral connection of the four plastic films in accordance with step (a).

4. A method in accordance with claim 3, wherein the filling of the upper and/or lower chambers in accordance with step (b) takes place through the interruption.

5. A method in accordance with claim 1, wherein the crosslinking of the silicone compound takes place by increasing temperature.

6. A method in accordance with claim 1, additionally comprising a step of introducing a medium for reducing adhesive tendency of the oppositely disposed inner surfaces of the shell bodies (10, 20) bodes into the fluid space (30).

7. A method in accordance with claim 6, wherein the medium for reducing the adhesive tendency of the oppositely disposed inner surfaces of the shell bodies (10, 20) is introduced before the filling of the upper and lower chambers with a crosslinkable silicone compound in accordance with step (b).

8. A method in accordance with claim 6, wherein the medium for reducing the adhesive tendency of the oppositely disposed inner surfaces of the shell bodies (10, 20) is introduced between the filling of the upper and lower chambers with a crosslinkable silicone compound in accordance with step (b) and the crosslinking of the silicone compound in accordance with step (c).

9. A method in accordance with claim 6, wherein the medium for reducing the adhesive tendency of the oppositely disposed inner surfaces of the shell bodies (10, 20) is introduced after the crosslinking of the silicone compound in accordance with step (c).

10. A method in accordance with claim 1, wherein the valve tube (40) is inserted to externally extend into the fluid space (30) beyond a connection region between the first and second shell bodies (10, 20).

11. A method in accordance with claim 10, wherein the valve tube (40) is composed of flexible material and provided with a check valve to allow the user to subsequently fill and empty the fluid space (30), after production.

12. A method in accordance with claim 11, wherein the plastic films are peripherally welded together to form a peripheral weld seam (15) between the first and second shell bodies (10, 20), and
the valve tube (40) penetrates the weld seam (15) in a radial direction, extends up to an end of the weld seam (15), projects freely into the fluid space (30) without being connected to one of the first and second shell bodies (10, 20) beyond the weld seam (15), and is freely movable within the fluid space (30).

13. A method in accordance with claim 6, wherein the medium for reducing the adhesive tendency of the oppositely disposed inner surfaces of the shell bodies (10, 20) is introduced into the fluid space (30) through the valve tube (40).

14. A method in accordance with claim 11, wherein the check valve is a flutter valve.

15. A method in accordance with claim 1, wherein the valve tube (40) is adhesively bonded or welded between the two middle films and penetrates a weld or adhesive seam between the films in a radial direction.

\* \* \* \* \*